United States Patent
Zhu et al.

(10) Patent No.: US 10,085,991 B2
(45) Date of Patent: Oct. 2, 2018

(54) FORMULATION INHIBITING EFFECTS OF LOW ACID ENVIRONMENT

(71) Applicants: Merck Sharp & Dohme Corp., Rahway, NJ (US); Lei Zhu, Basking Ridge, NJ (US); Yvonne Cegielnik, Roseland, NJ (US); Qun Lu, Berkeley Heights, NJ (US)

(72) Inventors: Lei Zhu, Basking Ridge, NJ (US); Yvonne Cegielnik, Roseland, NJ (US); Qun Lu, Berkeley Heights, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/532,721

(22) PCT Filed: Dec. 1, 2015

(86) PCT No.: PCT/US2015/063060
§ 371 (c)(1),
(2) Date: Jun. 2, 2017

(87) PCT Pub. No.: WO2016/089796
PCT Pub. Date: Jun. 9, 2016

(65) Prior Publication Data
US 2017/0354658 A1    Dec. 14, 2017

Related U.S. Application Data

(60) Provisional application No. 62/087,607, filed on Dec. 4, 2014.

(51) Int. Cl.
| | | |
|---|---|---|
| A61K 31/52 | (2006.01) |
| A61K 9/00 | (2006.01) |
| A61K 47/26 | (2006.01) |
| A61K 47/02 | (2006.01) |
| A61K 47/20 | (2006.01) |
| A61K 47/12 | (2006.01) |
| A61K 47/32 | (2006.01) |
| A61K 9/10 | (2006.01) |
| A61K 47/38 | (2006.01) |

(52) U.S. Cl.
CPC ............ *A61K 31/52* (2013.01); *A61K 9/0053* (2013.01); *A61K 9/10* (2013.01); *A61K 47/02* (2013.01); *A61K 47/12* (2013.01); *A61K 47/20* (2013.01); *A61K 47/26* (2013.01); *A61K 47/32* (2013.01); *A61K 47/38* (2013.01)

(58) Field of Classification Search
None
See application file for complete search history.

(56) References Cited

U.S. PATENT DOCUMENTS

| 8,389,532 B2 * | 3/2013 | Boyle ................. C07D 487/14 514/267 |
| 2004/0110694 A1 | 6/2004 | Ghebre-Sellassie et al. |
| 2007/0072867 A1 | 3/2007 | Boyle et al. |
| 2012/0064157 A1 | 3/2012 | Dokou et al. |
| 2012/0225118 A1 | 9/2012 | Chen et al. |

FOREIGN PATENT DOCUMENTS

WO   WO2013040187 A1   3/2013

OTHER PUBLICATIONS

International Search Report—dated Jan. 13, 2016.

* cited by examiner

*Primary Examiner* — Brian J Davis
(74) *Attorney, Agent, or Firm* — H. Eric Fischer; John C. Todaro (57) ABSTRACT

The present invention is directed to formulations comprising PVP polymer, a dispersion of a compound of Formula I (API), and citric acid, which formulations mitigate the effects of coadministering the compound of Formula I with a proton pump inhibitor compound.

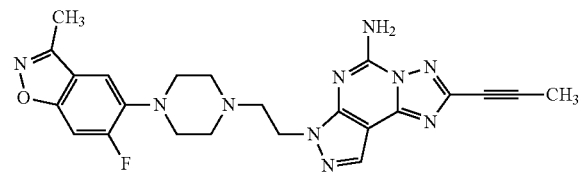

16 Claims, 3 Drawing Sheets

FORMULATION INHIBITING EFFECTS OF LOW ACID ENVIRONMENT

CROSS-REFERENCE TO RELATED APPLICATIONS

This application is the national stage entry of International Patent Application Serial No. PCT/US2015/063060, filed Dec. 1, 2015, which in turn claims the priority of U.S. provisional application Ser. No. 62/087,607 filed Dec. 4, 2014, which applications are incorporated herein in their entirety by reference thereto.

BACKGROUND

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2A}$, $A_{2b}$ and $A_3$. $A_1$ and $A_3$ are high-affinity, inhibiting the activity of the enzyme adenylate cyclase, and $A_{2A}$ and $A_{2b}$ are low-affinity, stimulating the activity of the same enzyme.

Analogs of adenosine able to interact as antagonists with the $A_1$, $A_{2A}$, $A_{2b}$ and $A_3$ receptors have also been identified. Selective antagonists for the $A_{2A}$ receptor are of pharmacological interest because of their reduced level of side effects. In the central nervous system, $A_{2A}$ antagonists can have antidepressant properties and stimulate cognitive functions. Moreover, data has shown that $A_{2A}$ receptors are present in high density in the basal ganglia, known to be important in the control of movement. Hence, $A_{2A}$ antagonists can improve motor impairment due to neurodegenerative diseases, for example, Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2A}$ affinity with varying degrees of $A_{2A}$ vs. $A_1$ selectivity. Triazolo-pyrimidine adenosine $A_{2A}$ receptor antagonists with different substitution at the 7-position have been disclosed previously, for example in WO 95/01356; U.S. Pat. No. 5,565,460; WO 97/05138; and WO 98/52568.

Parkinson's disease is characterized by progressive degeneration of the nigrostriatal dopaminergic pathway. The subsequent reduction in striatal dopamine levels is responsible for motor symptoms associated with Parkinson's disease, e.g., the loss of fine motor control or motor impairment manifested in those suffering from the disease. Current methodologies for alleviating motor symptoms associated with Parkinson's disease seek to replace dopamine either within the presynaptic terminal, for example, by administration of L-Dopa, directly through stimulation of the postsynaptic $D_2$ receptors, or by inhibiting metabolism, for example, by administration of monoamine oxidase type B (MAO-B) or catechol-O-methyltransferase (COMT). Long term use of such therapies is often associated with adverse events. For example, long term therapy with L-Dopa (currently the standard of care) is often associated with adverse events (e.g. motor complications), for example, "wearing-off", "random on-off" oscillations, or dyskinesia. These motor complications arising from therapy administered to manage Parkinson's disease often become progressively more severe with continued treatment.

As mentioned above, $A_{2A}$ receptors are present in high density in the basal ganglia and are known to be important in the control of fine motor movement. Highly selective $A_{2A}$ antagonists have demonstrated their efficacy in reducing motor symptoms associated with neurodegenerative diseases. Accordingly, compounds which are $A_{2A}$ receptor antagonists are believed to be useful in alleviating motor symptoms associated with Parkinson's disease. For example, U.S. Pat. No. 8,389,532 to Boyle et al. (the '532 patent) describes the preparation of the compound of Formula I:

Formula I

In the '532 patent, Example 1 shows methods of preparing compounds of Formula I, and describes also that the compound of Formula I can be prepared as a pharmaceutically acceptable salt which may be useful for treating Parkinson's disease.

Patients suffering from Parkinson's disease generally suffer from gastric disorders related to over-production of stomach acid, for example, acid reflux and GERD. Accordingly, it is common among patients suffering from Parkinson's disease to be on a course of medication to address such issues, for example, a proton pump inhibitor, for example pantoprazole, omeprazole or ranitidine. Desirably, the compound of Formula I for use in providing treatment of Parkinson's disease symptoms requires that it be formulated in a manner that it can be provided as an orally administered tablet compatible with other medications commonly in use in the treatment of symptoms of Parkinson's disease.

SUMMARY OF THE INVENTION

In one aspect, the invention provides a formulation mitigating the effects of coadministered ppi therapy in patients to being treated with the A2a-inhibitor of Formula I, the formulation comprising:
(a) a dispersion comprising:
  (i) a water soluble matrix polymer;
  (ii) a compound of Formula I:

Formula I and
(iii) citric acid,
wherein, at least about 70 mole % of said compound of Formula I is present in the dispersion in the form of a citrate salt; and (b) a mixture of at least one acidifying agent and at least one solubilizing agent.

In some embodiments of the inventive formulation, it is preferred for the citric acid in said dispersion comprising a compound of Formula I to form an amorphous citrate salt with more than about 95 mole % of the compound of Formula I present therein, and more preferably, to form an amorphous citrate salt with about 100 mole % of the compound of Formula I present therein.

In some embodiments of the inventive formulation, it is preferred for the dispersion to comprise up to about 30 wt. % of a compound of Formula I, including the amount which converts to an amorphous citrate salt during preparation, up to about 20 wt. % of citric acid, including the amount present in the citrate salt of the compound of Formula I, and the balance of the weight of said dispersion to be a water soluble matrix polymer, preferably polyvinylpyrolidone/vinyl acetate (PVP-VA) copolymer.

In some embodiments it is preferred for the acidifying agent in the mixture of at least one acidifying agent and at least one solubilizing agent to be citric acid. In some embodiments it is preferred for the solubilizing agent in the mixture of at least on acidifying agent and at least one solubilizing agent to be sodium lauryl sulfate.

In some embodiments it is preferred to provide a formulation suitable for capsule fill, said formulation comprising:
(a) about 40 wt. % of a dispersion comprising:
  (i) from about 2.5 wt % of a compound of Formula I to about 12 wt. % of a compound of Formula I wherein, at least about 95 mole % of the compound of Formula I is in the form of a citrate salt;
  (ii) citric acid; and
  (iii) a matrix polymer;
(b) about 7 wt. % of a mixture of sodium lauryl sulfate and crospovidone which are present in the mixture in a wt. ratio of 2:5 sodium lauryl sulfate:crospovidone;
(c) about 12 wt. % of anhydrous citric acid not including that which is used in the dispersion;
(d) about 1 wt. % of colloidal silicon dioxide;
(e) about 2 wt. % of stearic acid; and
(f) the balance of the weight of said formulation mannitol.

In one aspect the invention provides a formulation for use in treating movement disorders associated with Parkinson's disease. In one aspect the invention provides A2a-antagonist therapy to patients in need thereof who are also receiving proton-pump inhibiting therapy, said method comprising orally administering a therapeutic amount of a formulation of the invention to a patient in need thereof.

DETAILED DESCRIPTION OF THE INVENTION

As mentioned above, the present invention is directed to a formulation which permits the coadministration of proton pump inhibitors and the compound of Formula I, the bioavailability of which would be impaired by the low acid levels induced with the use of proton pump inhibitors. The impact of low stomach acid environment on the bioavailability of the compound of Formula I is illustrated in Table I. In generating this data, equivalent tablets were pressed from a mixture comprising the compound of Formula I, mannitol, hydroxypropyl cellulose, microcrystalline cellulose, and magnesium stearate, which mixture was prepared using a high shear wet granulation process. Tablets were pressed to equal hardness from this mixture and coated with Opadry® II Y-30. Thus prepared, the tablets contained the equivalent of 40 mg of the Compound of Formula I. These tablets were administered orally to healthy human volunteers alone or coadministered with a pantoprazole proton pump inhibitor (Protonix®) and the serum levels of the compound of Formula I were observed following administration. The data obtained are presented in Table I.

TABLE I

| Treatment | Parameter | Least Squares Mean (LSM) | LSM (standard error) | Geometric mean (LS) |
|---|---|---|---|---|
| Reference Tablet Without Coadmin PPI | Ln $AUC_{0-\infty}$ hr * ng/mL | 7.6383 | 0.2591 | 2076.2405 |
| | Ln $AUC_{last}$ hr * ng/mL | 7.5749 | 0.2653 | 1984.7036 |
| | Ln $C_{maxt}$ ng/mL | 4.7940 | 0.2823 | 120.7810 |
| Reference Tablet with PPI | Ln $AUC_{0-\infty}$ hr * ng/mL | 6.3442 | 0.2769 | 569.1996 |
| | Ln $AUC_{last}$ hr * ng/mL | 6.1277 | 0.2653 | 458.3905 |
| | Ln $C_{max}$ ng/mL | 3.3713 | 0.2823 | 29.1159 |

As reflected in the data presented in Table I, the ratio of (Ln $AUC_{0-\infty}$) values (with PPI coadministration/without PPI) is 0.2741 (CI 90% lower=0.1400, CI 90% Upper=0.5367), the ratio of (Ln $AUC_{last}$) values (with PPI coadministration/without PPI) is 0.2352 (CI 90% lower=0.1215, CI 90% Upper=0.4555) and the ratio of (Ln $C_{max}$) values (with PPI coadministration/without PPI) is 0.2411 (CI 90% lower=0.1193, CI 90% Upper=0.4871). These data reflect that there is a significant reduction in bioavailability when a proton pump inhibitor is present at the time of administration.

An attempt to mitigate the effect of a proton pump inhibitor (ppi) on bioavailability by increasing the amount of the compound of Formula I present in a dosage form comprising the compound of Formula I not only decreases safety margins but presents the strong possibility of great variability between patients and a significant risk of overdosing a particular patient.

Accordingly, the present invention provides compositions suitable for preparing a tablet of acceptable strength, comprising a solid dispersion of the compound of Formula I, wherein a substantial mole fraction of the compound of Formula I present in the dispersion has been converted to a citrate salt. In general, the dispersion used in preparing capsule formulations of the invention are produced by spray-drying, however it will be appreciated that any means of converting a substantial amount of a compound of Formula I into the corresponding citrate salt dispersed in a polymer matrix may be employed.

In general, solid dispersions of the present invention (also referred to as an amorphous dispersion) comprise a polymer matrix with the compound of Formula I in the form of a citrate salt (API) in an amorphous, highly dispersed state, or dissolved in the polymer to form a solid solution. In general such solid dispersions include also additional components to aid in the dispersion/dissolution of the API or the stability of the composition, for example, a surfactant or a fluxing agent. The dispersions are stable, and the compound of Formula I does not form crystals or other insoluble particles. As the term is used herein, "dispersion" contemplates "solid solutions", "molecular dispersions", and fine suspensions of one moiety within a polymer matrix, such as are produced by the processes described below.

Such methods include preparing a solution or suspension of the API and the matrix polymer and spray-drying it, as well as wet granulation of the API-containing dispersion blended with other excipients necessary for preparing the final dosage form, using wet granulation if necessary and conventionally drying and screening the granulated mixture. Processes for preparing capsule formulations are well known in the art.

For an example of spray drying technique, see, e.g., Masters, Spray Drying Handbook, 1991, 5$^{th}$ edition, Longman Scientific & Technical, and, as practiced in a variety of industrial applications including spray drying of pharmaceutical products (see, e.g., U.S. Pat. No. 6,763,607). Generally, in spray drying, the matrix polymer, API, and other excipients as needed, for example, a surfactant, are dissolved in a solvent and are then sprayed through a nozzle as a fine spray into a chamber (generally with a current of heated air or gas passing through) where the solvent is evaporated quickly to make particles comprising polymer, drug, and any other excipients present in the solution/suspension being spray dried. Ideally, the solvent is selected to dissolve at least the matrix polymer and most or all of other components, and which has sufficiently high vapor pressure in the spray drier chamber environment that it is readily evaporated. The solvent should also be suitable for use in preparing pharmaceutical compositions. In some applications it has been known to use a mixed solvent systems, particularly those containing a combination of water and a volatile solvent, as necessary to facilitate the production of a suitable solid dispersion comprising the API. Examples of useful volatile solvents for spray drying include acetone, ethanol, methanol, isopropanol and tetrahydrofuran (THF). An exemplary mixed solvent system is acetone:water (90:10). Further example of mixed solvent systems is described in International Patent Application Publication No. WO2007/109605 and in U.S. Patent Application Publication No. US2007/0026083.

Following formation of a solid dispersion, the resulting spray dried intermediate can undergo a secondary drying step to remove residual solvents. This secondary drying unit operation can occur in a static dryer, for example a tray dryer, or agitated dryer. Gas, humidified gas, or vacuum may be applied to the material in the secondary dryer and such application can be useful in more rapidly removing residual solvents that remain in the spray dried intermediate. See, e.g., European Patent Application No. EP1855652 A2 (and references therein) and International Patent Application Publication No. WO2008012617A1 (and references therein).

Formulations of the invention used in preparation of oral dosage forms (i.e., tablets or capsules) may further comprise other excipients. For example: a typical formulation of the invention directed to the preparation of a pressed tablet may contain a diluent (for example, mannitol, article of commerce, and/or microcrystalline cellulose, for example Avicel®); a glidant (for example, colloidal silica, for example Cab-O-Sil®); a disintegrant, for example, crospovidone, and a lubricant (for example, sodium stearate, article of commerce). It will be appreciated that in formulating compositions of the invention, other diluents, glidants, disintegrants and lubricants may be substituted to effect similar formulations.

The following definitions apply to excipients which may be used in formulations of the invention. Often, some excipients perform more than one of the defined functions in a tablet formulation, as will be appreciated:

a diluent is an excipient which increase the bulk of a dosage form, typically where the active pharmaceutical ingredient in the formulation is too potent to permit convenient processing or administration of a dosage form which does not include a diluent, or where the formulation by itself without a diluent makes formation of the dosage form difficult (for example, where an aliquot of the formulation without a diluent would be of too small of a volume to form the aliquot into a tablet);

a disintegrant is an excipient that expands and/or dissolves when placed in an aqueous environment, for example, the gastrointestinal tract, which aids a tablet in breaking apart and promotes release of an active pharmaceutical ingredient contained in a tablet;

a Glidant is an excipient, for example colloidal silica, that enhances the flow of a granular mixture by reducing inter-particle friction.

Pharmaceutical formulations intended for the preparation of oral dosage forms (tablets and capsules) may further contain one or more agents selected from the group consisting of sweetening agents, flavoring agents, coloring agents and preserving agents in order to provide pharmaceutically elegant and palatable preparations.

Pharmaceutical formulations intended for the preparation of oral dosage forms (tablets and capsules) may further contain one or more agents selected from the group consisting of sweetening agents, flavoring agents, coloring agents and preserving agents in order to provide pharmaceutically elegant and palatable preparations.

Compositions for use in capsules (e.g., hard gelatin) may contain in addition to the composition of the invention, inert solid diluent, for example, calcium carbonate, calcium phosphate or kaolin, or as soft gelatin capsules wherein the active ingredient is mixed with liquids or semisolids in which the composition of the invention, or the API therein, is not soluble, for example, peanut oil, liquid paraffin, fractionated glycerides, surfactants or olive oil.

In the preparation of formulations of the invention suitable for use in the preparation of solid oral dosage forms comprising a composition of the invention, the composition of the invention and other excipients may be blended, roller compacted or wet granulated to densify and/or reduce the risk of segregation of components during subsequent handling (e.g., compression into tablets or capsule filling). Granulation steps can also be used to minimize the impact of raw material property variability (e.g., excipient particle size) on subsequent processing (e.g., capsule filling) and ultimate product performance. Lubrication is typically performed prior to roller compaction and tablet compression to reduce the tendency of material to adhere to compression surfaces (e.g., milling or sieving surfaces in various processing equipment employed to process formulations and fill capsules or press tablets). In general lubricants are derivatives of stearic acid, for example, magnesium stearate or sodium stearyl fumarate. Techniques and methods useful in preparation of dosage forms are known, for example, as described in Ansel, Introduction to Pharmaceutical Dosage Forms, Seventh Edition, 1999.

In general, preparation of oral dosage forms from pharmaceutical formulations of the invention requires that the pharmaceutical formulation of the invention (admixture of excipients, disintegrating system and composition of the invention) is rendered into a single-dose compatible form, for example, an aliquot of suitable amount encapsulated in capsule (e.g., using hard gelatin capsules). Techniques suitable for preparing solid oral dosage forms for encapsulation are generally described in Remington's Pharmaceutical Sciences, 18th edition, edited by A. R. Gennaro, 1990, Chapter 89 and in Remington—The Science and Practice of Pharmacy, 21st edition, 2005, Chapter 45.

As mentioned above, the present invention is a dispersion comprising the compound of of Formula I in the form of an amorphous citrate salt (active pharmaceutical ingredient or "API" herein) and citric acid dispersed in a matrix polymer. Suitable matrix polymers for compositions of the invention include water-soluble polymers, for example PVP polymer which is made by free-radical polymerization of a 6:4 ratio of vinylpyrrolidone:vinyl acetate monomer, for example, the polyvinylpyrrolidone/vinylacetate copolymer sold under the trade name Kollidon® 64, and equivalents thereof. Additionally, in some embodiments, a water-soluble cellulosic polymer may be employed as the matrix polymer, for example, alkylcelluloses (e.g., methylcellulose or ethylcellulose) and hydroxyalkylcelluloses (e.g., hydroxypropylcellulose), hydroxyalkylalkylcelluloses (e.g., hydroxypropylmethylcellulose).

It will be appreciated that other polymers and blends of polymers may also be adapted to a composition of the invention.

Suitable anhydrous citric acid for use in compositions of the invention is an article of commerce meeting the standards acceptable for use in oral medications, for example, citric acid (anhydrous) from ADM, Paris, Ky.

In general, a dispersion, or a formulation for capsule fill or tableting made therewith, can include also a surfactant or solubilizing agent. Thus, along with an aliquot of a dispersion of the invention, pharmaceutical formulations of the present invention may optionally comprise one or more surfactants. As is known in pharmaceutical formulation, surfactants can fill a number of roles, for example, they can increase the rate of dissolution by facilitating wetting, thereby increasing the maximum concentration of dissolved drug. The surfactants may also make the formulation easier to process. Surfactants may also stabilize the amorphous dispersions by inhibiting crystallization or precipitation of the drug by interacting with the dissolved drug by such mechanisms as complexation, formation of inclusion complexes, formation of micelles, and adsorption to the surface of the solid drug. Surfactants may also facilitate absorption of APIs by altering API permeability and/or efflux directly. See, e.g., Yu et al., Pharm Res, 1999, 16:1812-7. Non-limiting examples of pharmaceutically acceptable surfactants that are suitable for the present invention include polyoxyethylene castor oil derivates, e.g. polyoxyethyleneglycerol triricinoleate or polyoxyl 35 castor oil (CREMOPHOR® EL; BASF Corp.) or polyoxyethyleneglycerol oxystearate such as polyethylenglycol 40 hydrogenated castor oil (CREMOPHOR® RH 40, also known as polyoxyl 40 hydrogenated castor oil or macrogolglycerol hydroxystearate) or polyethylenglycol 60 hydrogenated castor oil (CREMOPHOR® RH 60); or a mono fatty acid ester of polyoxyethylene sorbitan, such as a mono fatty acid ester of polyoxyethylene (20) sorbitan, e.g. polyoxyethylene (20) sorbitan monooleate (Tween 80), polyoxyethylene (20) sorbitan monostearate (Tween 60), polyoxyethylene (20) sorbitan monopalmitate (Tween 40), or polyoxyethylene (20) sorbitan monolaurate (Tween 20). Other non-limiting examples of suitable surfactants include polyoxyethylene alkyl ethers, e.g. polyoxyethylene (3) lauryl ether, polyoxyethylene (5) cetyl ether, polyoxyethylene (2) stearyl ether, polyoxyethylene (5) stearyl ether; polyoxyethylene alkylaryl ethers, e.g. polyoxyethylene (2) nonylphenyl ether, polyoxyethylene (3) nonylphenyl ether, polyoxyethylene (4) nonylphenyl ether, polyoxyethylene (3) octylphenyl ether; polyethylene glycol fatty acid esters, e.g. PEG-200 monolaurate, PEG-200 dilaurate, PEG-300 dilaurate, PEG-400 dilaurate, PEG-300 distearate, PEG-300 dioleate; alkylene glycol fatty acid mono esters, e.g. propylene glycol monolaurate (lauroglycol, such as lauroglycol FCC); sucrose fatty acid esters, e.g. sucrose monostearate, sucrose distearate, sucrose monolaurate, sucrose dilaurate; sorbitan fatty acid mono esters such as sorbitan mono laurate (Span 20), sorbitan monooleate, sorbitan monopalmitate (Span 40), or sorbitan stearate; D-alpha-tocopheryl polyethylene glycol 1000 succinate (vitamin E TPGS); or a combination or mixture thereof. Other suitable surfactants include, but are not limited to, block copolymers of ethylene oxide and propylene oxide, also known as polyoxyethylene polyoxypropylene block copolymers or polyoxyethylene polypropyleneglycol, such as POLOXAMER® 124, POLOXAMER® 188, POLOXAMER® 237, POLOXAMER® 388, or POLOXAMER® 407 (BASF Corp.). In some embodiments of formulations of the present invention, one preferred solubilizing agent is sodium lauryl sulfate.

The following terminology, which may be used herein, is used in accordance with the following definitions.

Unless expressly stated to the contrary, all ranges cited herein are inclusive; i.e., the range includes the values for the upper and lower limits of the range as well as all values in between. As an example, temperature ranges, percentages, ranges of equivalents, and the like described herein include the upper and lower limits of the range and any value in the continuum there between.

The term "formulation", as used herein, refers to a blend, aggregation, solution or other combination of materials which includes an active pharmaceutical ingredient (API) which formulation is adapted to a particular mode of administration, for example, a formulation suitable for filling into capsules designed for oral administration, in the treatment, management, prevention and etc. of a disease state or condition in a patient.

The term "subject" as used herein refers to an animal, preferably a mammal, most preferably a human, who has been the object of treatment, observation or experiment. When a human subject suffering from the condition to be treated is included in the activity they are alternatively referred to herein as a "patient".

As mentioned, dispersions of the present invention comprise citric acid, an API of Formula I and a polymer, preferably a matrix polymer, wherein at least 70% of the compound of Formula I has formed an amorphous citrate salt in the dispersion, and in some embodiments, preferably, about 95 mole %, more preferably about 100 mole % of the compound of Formula I has formed amorphous citrate salt stabilized within in the dispersion. Without wanting to be bound by theory, it is believed that the amorphous salt of the compound of Formula I which is formed is stabilized by being dispersed in the polymer matrix such that while being readily available and providing a dissolution environment in which the effects of a proton pump inhibitor are neutralized, the material is also not subject to decomposition as it would be if only the unstabilized citrate salt were present. Desirably, formulations of the invention contain citric acid in excess of the amount required to form amorphous citrate salt with the compound of Formula I.

Without wanting to be bound by theory, it is believed that the dispersion provides upon dissolution of an oral dosage form made from a formulation comprising the dispersion (for example, a capsule, as described below, or a tablet), a local environment at the point of dissolution which has sufficient acidity levels to permit release of the compound of Formula I from the dosage form and into a patients GI tract for absorption.

Figure 1:
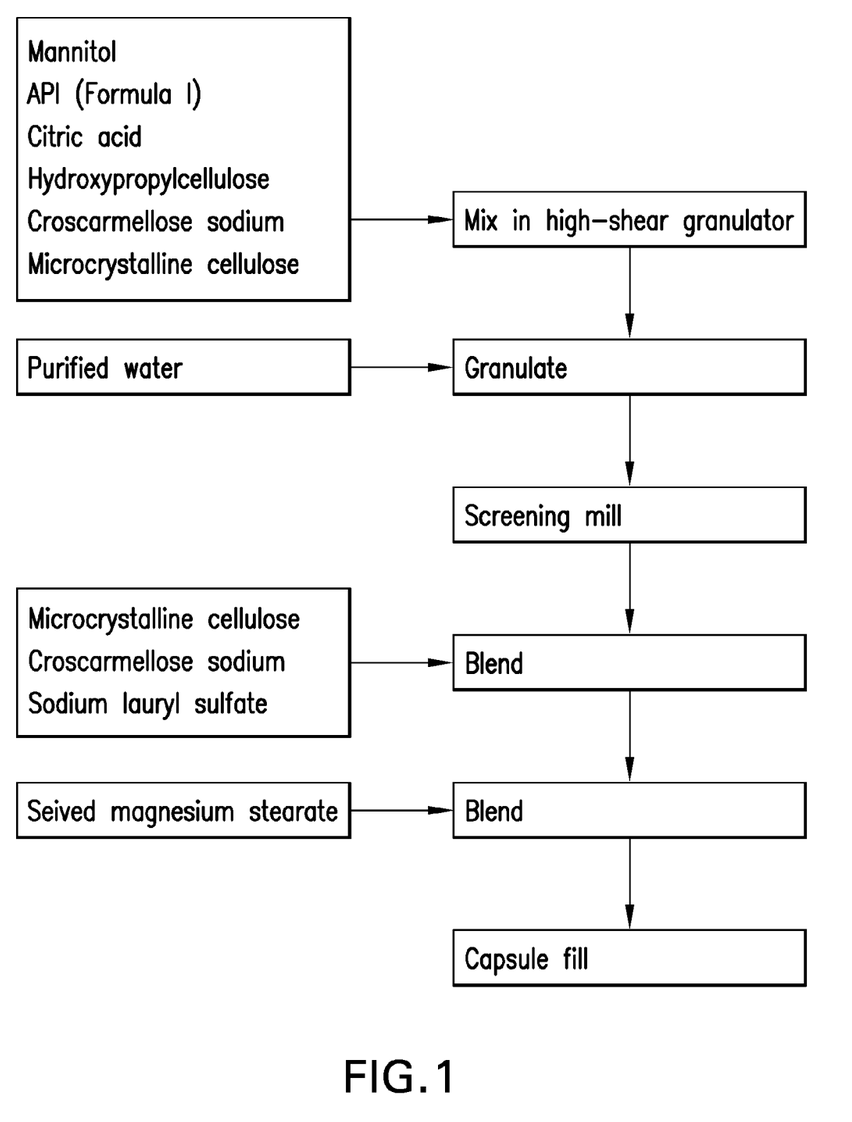
FIG. 1: Flow Chart for Preparing Wet-granulated dispersion of amorphous citrate salt of the compound of Formula I.

With reference to FIG. 1, a granulated dispersion was prepared in accordance to the process diagram shown, which dispersion contains about 70 mole % of the compound of Formula I converted to an amorphous citrate salt.

EXAMPLE I

Preparation of a Dispersion Comprising the Compound of Formula I with 70% Citric Acid Formation and a Capsule-Fill Formulation Prepared Therefrom The granulated dispersion was prepared in accordance with the following procedure:

1. Into a high-shear granulator was charged mannitol, the compound of Formula I, citric acid anhydrous, hydroxypropylcellulose, croscarmellose sodium and microcrystalline cellulose in the amounts shown in Table II (batch weight was 12 Kg which was granulated with 610 g of water). The granulator was operated mix for 5 minutes using an impeller speed of 125 rpm and a chopper speed of 1050 rpm to mix the excipients.
2. The dry mix from Step 1 was granulated using purified water, added at an addition rate of 90 g/min until 610 g is added, an impeller speed of 125 rpm and a chopper speed of 1050 rpm and granulated for 2 minutes.
3. The wet granulation prepared in Step 2 was passed through a screening mill equipped with a 0.375 inch screen and an impeller speed of 1350 rpm.
4. The screened granulate from Step 3 was placed in a tray dryer and dried using a temperature of 43° C. for 20 hours to a loss on drying of ≤2.0%.
5. The granulate dried in Step 4 was screened through a screening mill equipped with a 0.04" screen and an impeller speed of 1350 rpm.
6. The milled granulate from Step 5 and the remainder of the microcrystalline cellulose, croscarmellose sodium and sodium lauryl sulfate were placed in a diffusion blender and blended for 250 revolutions.
7. Magnesium stearate was passed through a suitable screen; then charged into the mixture in the blender prepared in Step 6 and the charge was blended for an additional 45 revolutions to make the final blend.

Table II, below, reflects the amount of material which was used in making the formulation described above.

TABLE II

| Constituent | Standard | Amount |
| --- | --- | --- |
| Compound of Formula I | As prepared in house | 300 g |
| Anhydrous Citric Acid | USP | 3600 g |
| Mannitol | USP | 3660 g |
| hydroxypropylcellulose | NF | 360 g |
| Microcrystalline cellulose | NF | 2970 g |
| Croscarmellose Sodium | NF | 720 g |
| Sodium Lauryl Sulfate | NF | 300 g |
| Magnesium Stearate | NF | 0 g |

The formulation of Example I was hand-filled into capsules at the point of use for use in a Human PK study in accordance with the following procedure:

1. Weigh an empty size "0" hard gelatin capsule shell.
2. Record the weight ($W_{empty\ capsule}$).
3. Weigh 400.00 mg±2.0% (range: 392.00-408.00 mg) of the wet-granulate dispersion prepared above on a weigh paper.
4. Record the weight.
5. Separate the cap and body of the capsule. Place the capsule body in the holder of a suitable Torpac®.
6. Place the Torpac® funnel over the capsule body in the holder.
7. Transfer the weighed the wet-granulate dispersion prepared in Step 3 into the funnel.
8. Use the Torpac® tamper to gently tap the funnel to make sure all the material gets into the capsule body.
9. Use the tamper to gently compress the filling material into capsule body.
10. Slowly remove the funnel.
11. Place the capsule's cap onto the body of the capsule, pressing firmly to lock.
12. Remove the filled capsule from the base.
13. Weigh the filled capsule ($W_{filled}$ capsule).
14. Record the weight.
15. Calculate the weight of the filled material ($W_{filled\ material}$) using the following equation: $W_{filled\ material} = W_{filled\ capsule} - W_{empty\ capsule}$
16. Make sure $W_{filled\ material}$ is within 400.00 mg±2.0% (392.00-408.00 mg) range.
17. Place the filled capsule into a labeled HDPE bottle and securely close it. Store the HDPE bottle at refrigerated condition (2-8° C.) until use.

The amount of the formulation filled into hard gelatin capsules provided the equivalent of a 10 mg aliquot of the freebase compound of Formula I. Four capsules (together containing the equivalent of 40 mg of the free base compound of Formula I) were administered to healthy human volunteer subjects either with contemporaneous administration of pantoprazole or without administration of pantoprazole, and the serum levels of the compound of Formula I were monitored.

The data obtained from this study are summarized in Table III, below. These data reflect that the formulation comprising about 70 mole % conversion of the compound of Formula I to the citrate salt eliminates the adverse effect of coadministration of a proton pump inhibitor and a medicament comprising the compound of Formula I. As is shown in the next example, the formulation comprising a spray-dried dispersion where about 100% of the compound of Formula I is converted to an amorphous citrate salt also provides satisfactory PK performance when studied in famotidine-treated dogs and is believed to have increased stability.

TABLE III

| Parameter | TRT | Subject no | LS Mean | 95% Ci (of GM) | E/B GMR | 90% Ci of GMR |
| --- | --- | --- | --- | --- | --- | --- |
| $AUC_{0-\infty}$ | Without coadmin PPI | 14 | 8565.72 | 7351.35, 9980.70 | 1.06 | 0.97, 1.14 |
| $AUC_{0-\infty}$ | With coadmin PPI | 13 | 9037.18 | 7937.79, 10288.84 | | |
| $C_{max}$ | Without coadmin PPI | 14 | 584.65 | 494.73, 690.91 | 1.19 | 1.03, 1.37 |
| $C_{max}$ | With coadmin PPI | 13 | 695.3 | 615.23, 785.90 | | |

Aliquots of the material prepared above were analyzed using solid-state fluorine-19 nuclear magnetic resonance (NMR) spectroscopy. The fluorine-19 spectra were recorded on a Bruker Avance400 spectrometer, operating at a proton frequency of 400 MHz, and using a Bruker 4 mm HFX triple resonance CPMAS probe. The fluorine-19 spectra were collected utilizing 100 kHz proton 90° excitation pulses and SPINAL64 decoupling, proton/fluorine variable-amplitude cross-polarization (VACP) with the fluorine-19 cross-polarization power matched, a contact time of 1 ms, and a pulse delay of 45 s, while magic-angle spinning (MAS) the samples at 14 kHz. A line broadening of 100 Hz was applied to the fluorine-19 spectra before Fourier Transformation. Chemical shifts are reported using the fluorine in Teflon (−122.00 ppm.) as a secondary reference.

The ssNMR fluorine-19 CPMAS data were used to quantify the form of the compound of Formula I in the sample. The quantification of the amount of compound of Formula I in a particular form is based on the property of NMR data that peak areas are directly proportional to the amount of the respective components in the samples. Normalized CPMAS reference spectra of the relevant forms of the compound of Formula I are used to identify and quantify the respective forms. The results of the NMR measurements indicate that the material contains about 19 mole % crystalline Formula I-citrate salt, about 78 mole % amorphous Formula I-citrate salt and about 3 mole % crystalline citrate salt.

Analysis of the fluorine-19 CPMAS ssNMR data for these samples shows that about 80% and 3% of the compound of Formula I is present as amorphous and crystalline Citrate Salts, respectively. The limit of detection of the analysis is estimated based on the signal-to-noise ratio of the fluorine-19 CPMAS spectra to be approximately 1%.

Figure 2:
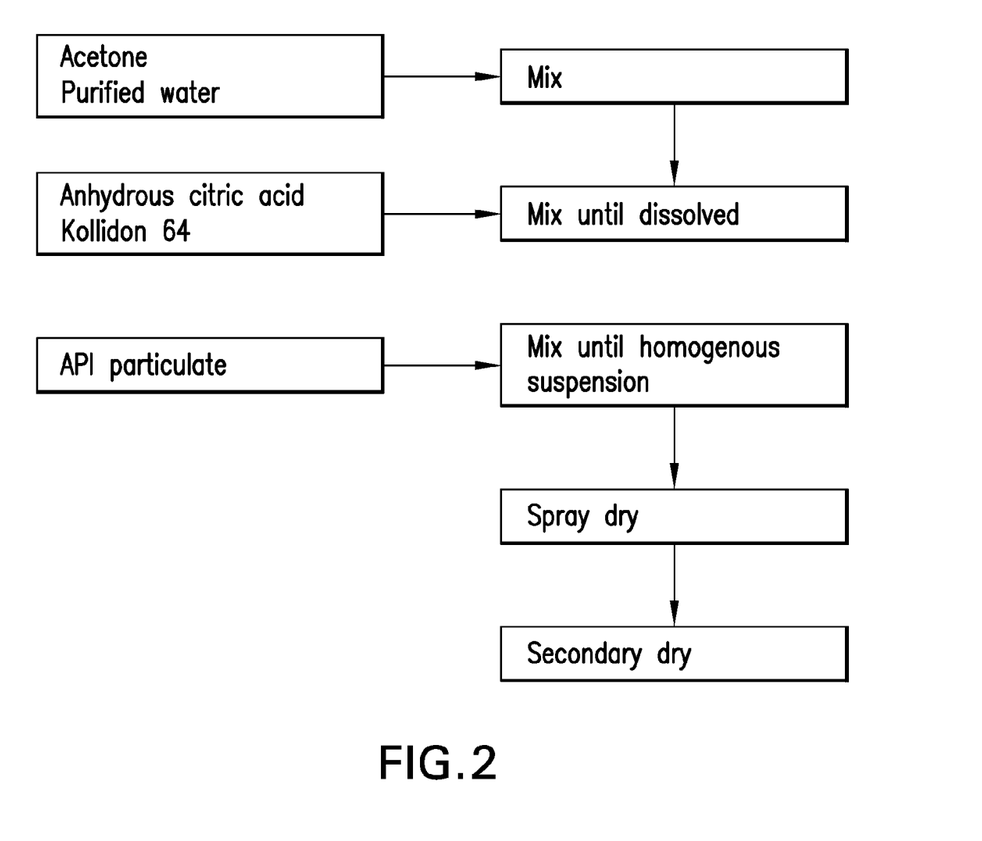
FIG. 2: Flow Chart for Spray-Dried dispersion of the invention.

With reference to FIG. 2, a dispersion of the invention in which about 100 mole % of the compound of Formula I is converted to a citrate salt dispersed in the matrix polymer was prepared in accordance with the process diagram shown by spray-drying technique.

PREPARATIVE EXAMPLE II

Preparation of a Dispersion Comprising Kollidon® 64 and the Compound of Formula I with about 100% Citric Salt Formation Spray drying was carried out by preparing a suspension of the compound of Formula I in a solution of citric acid anhydrous, PVP-VA64, acetone, and water, in the amounts shown in Table IV. The suspension was prepared in an agitated tank with an in-line recirculation loop and jet mixer to maintain the compound of Formula I in suspension with the citric acid/PVP-VA64 mixture in an 85:15 vol/vol, acetone/water mixed solvent.

Spray drying was conducted using PSD-1 spray dryer by GEA Process Engineering Inc. at Bend Research. A tube-in-tube heat exchanger was placed in-line directly before the nozzle to achieve the target solution temperature (115° C.) to ensure dissolution of the compound of Formula I into the solution before atomization. The solution flow rate was set at 125 g/min, $N_2$ flow rate at 1870 g/min, inlet and outlet temperature at 97° C. and 45° C. respectively. At these settings the residence time of the suspension in the heat exchanger is 15.7 seconds. The solution was spray-dried to provide a powder having a D(v,0.5)~10 µm.

The spray-dried material was collected and tray-dried at 40° C./to a dryness of 50% relative humidity to remove excess acetone from the spray dried solid dispersion.

TABLE IV

Table 1: Spray drying solution composition

| Component | Amount of material in Run |
| --- | --- |
| Compound of Formula I | 200 g |
| Citric acid anhydrous | 133 g |
| PVP-VA64 | 334 g |
| Acetone | 6520 g |
| Water | 1151 g |

Aliquots of the material prepared above were analyzed using solid-state carbon-13 nuclear magnetic resonance (NMR) spectroscopy both as prepared and following stability testing, the results of which are shown in Table IVa. The carbon-13 spectra were recorded on a Bruker Avance400 spectrometer, operating at a proton frequency of 400 MHz, and using a Bruker 4 mm HXY triple resonance CPMAS probe. The carbon-13 spectra were collected utilizing 100 kHz proton 90° excitation pulses and SPINAL64 decoupling, proton/carbon variable-amplitude cross-polarization (VACP) with the carbon-13 cross-polarization power matched, a contact time of 3 ms, and a pulse delay of 100 s, while magic-angle spinning (MAS) the samples at 13 kHz. A line broadening of 30 Hz was applied to the carbon-13 spectra before Fourier Transformation. Chemical shifts are reported on the TMS scale using the carbonyl carbon of glycine (176.70 ppm.) as a secondary reference.

The ssNMR 13C CPMAS data were used to quantify the form of the compound of Formula I present in the samples. The quantification of the compound of Formula I forms is based on the property of NMR data that peak areas are directly proportional to the amount of the respective components in the samples. Normalized reference spectra of the relevant forms of the compound of Formula I are used to identify and quantify the respective forms.

A portion of the sample analyzed was subjected to stability testing (40° C. at 75% relative humidity in sealed container with descant for one month).

TABLE Iva

| Sample | Crystalline Free-base Formula I | Amorphous Free-base Formula I | Crystalline Formula I citrate salt | Amorphous Formula I citrate salt |
| --- | --- | --- | --- | --- |
| As Prepared | Below Limit of detection | Below Limit of detection | Below Limit of detection | 100 mole % |
| 1 month stability testing | Below Limit of detection | Below Limit of detection | Below Limit of detection | 100 mole % |

Analysis of the ssNMR data obtained from aliquots of the material before and after stability testing shows that 100% of the compound of Formula I in both samples is present as amorphous citrate salt. The sample analyzed after 1-month stability testing appeared to contain the same amount of citrate salt in an amorphous state. The limit of detection of the analysis is estimated based on the signal-to-noise ratio of the CPMAS spectra to be approximately 5%.

As determined using the solid state NMR technique described above, the process described above produced a solid dispersion or solid solution of the compound of Formula I in polyvinylpyrolidone/polyvinyl acetate that has at least about 95 mole % (given the limits of detection, 100 mole %) of the compound of Formula I converted to the corresponding citrate salt which is dispersed in the polymer matrix.

EXAMPLE II

Figure 3:
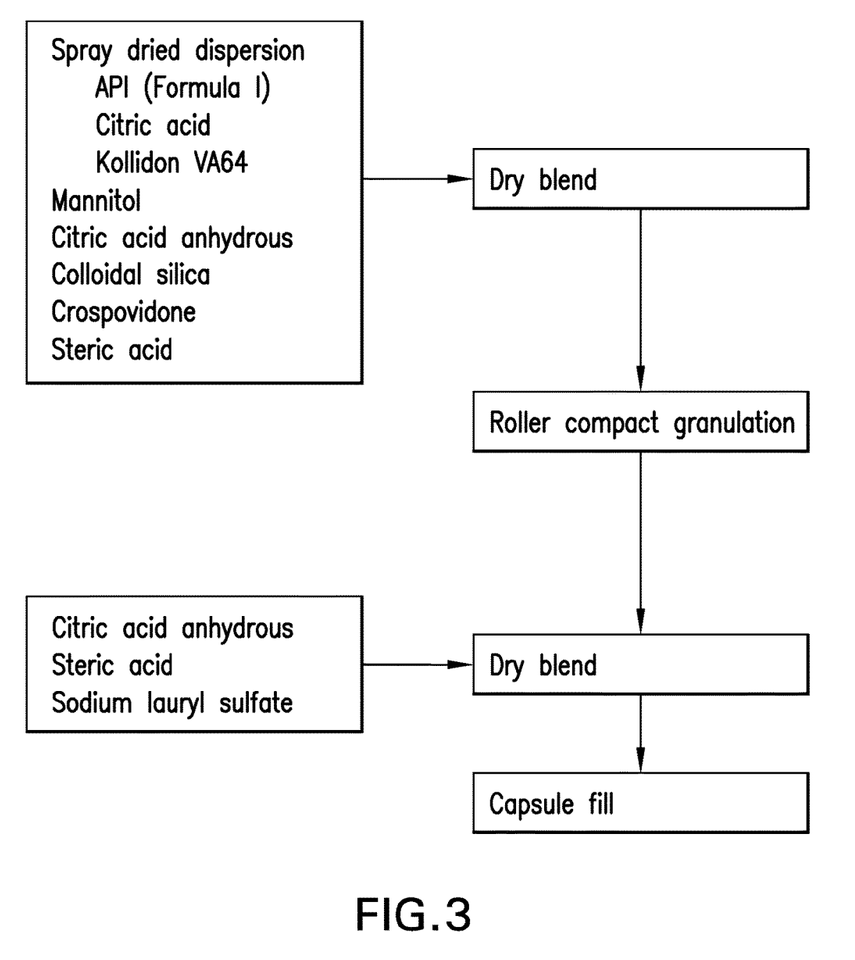
FIG. 3: Flow Chart for preparation of a Capsule Formulation comprising a Spray-Dried dispersion of the invention

Preparation of Formulations Comprising a Dispersion of the Compound of Formula I (100% Amorphose Citrate Salt) which is Suitable for Capsule Fill With reference to FIG. 3, a capsule fill formulation was prepared using the dispersion of Example II. Accordingly, the spray dried solid dispersion prepared in Example II (8.0 g) was dry granulated with mannitol (5.2 g), citric acid (2.4 g), crospovidone (1.0 g), colloidal silicon dioxide (0.2 g), and stearic acid (0.2 g) to give a "capsule" formulation having the relative weights of the excipients labelled "SDI Components" (extrudated) and "RC Intragranular" (excipients blended with the extrudated) shown in Table V) in a small slugging run (17 g total run weight), by roller compaction process to provide granules. Aliquots of 250 mg. of this formulation were filled into hard gelatin or HPMC capsules for use in study.

TABLE V

| Components | mg/Unit Strength |
|---|---|
| SDI Components | |
| API | 30 |
| Citric Acid | 20 |
| Kollidon ® VA 64 | 50 |
| RC Intragranular | |
| Mannitol, Compendial [SD 200] | 65 |
| Citric Acid Anhydrous | 30 |
| Crospovidone, Compendial | 12.5 |
| Colloidal Silicon Dioxide | 2.5 |
| Stearic Acid | 2.5 |
| RC Extragranular | |
| Citric Acid Anhydrous | 30 |
| Sodium Lauryl Sulfate | 5 |
| Stearic Acid | 2.5 |
| Size 1 Capsule (Gelatin or HPMC) | 1 unit |
| Capsule Fill Weight | 250 |

An aliquot of the Formulation prepared above was filled into size 1 hard gelatin capsules (Capsugel) that provided the equivalent of 5 mg aliquots of the compound of Formula I freebase. Single capsules were administered to beagle dogs which had been treated with famotidine contemporaneously (which is the equivalent of a 30 mg dosage in humans). Table VI summarizes the serum details from this study. These data indicate that an acceptable level of bioavailability is expected in humans who contemporaneously dose with a PPI inhibitor which is at least equivalent to the results observed from the formulation of Example I administered to humans which contained about 70 mole % conversion of the compound of Formula I to the corresponding citrate salt.

TABLE VI

| Formulation | $AUC_{(0-8)}$, µM * h | $C_{MAX}$, µM | $T_{MAX}$, h |
|---|---|---|---|
| Spray dried formulation | 0.386 ± 0.095 | 0.094 ± 0.034 | 1.04 ± 0.56 |

These Examples illustrate that the dispersion of the invention, when incorporated into a suitable formulation for oral administration, mitigates the adverse effects of coadministration of a proton pump inhibitor.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A formulation comprising:
   (a) a dispersion comprising:
      (i) a water soluble matrix polymer;
      (ii) a compound of Formula I:

Formula I and
      (iii) citric acid,
      wherein, at least about 70 mole % of said compound of Formula I is in the form of a citrate salt within the dispersion; and
   (b) a mixture of at least one acidifying agent and at least one solubilizing agent.

2. A formulation of claim 1, wherein said water soluble matrix polymer is polyvinylpyrolidone/vinyl acetate (PVP-VA) copolymer.

3. A formulation of claim 1, wherein at least about 95 mole % of the compound of Formula I present in the dispersion is in the form of amorphous citrate salt.

4. A formulation of claim 2, wherein about 100 mole % of the compound of Formula I present in the dispersion is in the form of amorphous citrate salt.

5. A formulation of claim 1, wherein said dispersion comprises:
   (a) about 50 wt. % of a 3:2 wt./wt. ratio of a compound of Formula I, including the amount which is converted to a citrate salt, and citric acid, including the amount present in the citrate salt of the compound of Formula I; and
   (b) the balance a water-soluble polyvinylpyrolidone/vinyl acetate copolymer.

6. A formulation of claim 1, wherein said water soluble matrix polymer is a water soluble cellulosic polymer.

7. A formulation of claim 1, wherein, the acidifying agent in the mixture of at least one acidifying agent and at least one solubilizing agent is citric acid.

8. A formulation of claim 1, wherein, the solubilizing agent in the mixture of at least one acidifying agent and at least one solubilizing agent is sodium lauryl sulfate.

9. A formulation of claim 1, wherein, said formulation comprises:

(a) about 40 wt. % of a dispersion comprising:
  (i) from about 2.5 wt % of a compound of Formula I to about 12 wt. % of a compound of Formula I wherein at least about 95 mole % of the compound of Formula I is in the form of a citrate salt within the dispersion;
  (ii) citric acid; and
  (iii) a water soluble matrix polymer;
(b) about 8 wt. % of a mixture of sodium lauryl sulfate and crospovidone which are present in the mixture in a wt. ratio of 2:5 sodium lauryl sulfate:crospovidone;
(c) about 12 wt. % of ex-dispersion anhydrous citric acid;
(d) about 1 wt. % of colloidal silicon dioxide;
(e) about 2 wt. % of stearic acid; and
(f) the balance of the weight of said formulation mannitol.

10. A formulation of claim 1, wherein the dispersion used in the formulation is prepared by heating a suspension of the compound of Formula I in a suspending solution comprising a mixed water/acetone solvent and citric acid to dissolve the compound of Formula I therein, and spray-drying the resulting heated solution.

11. A formulation of claim 1, wherein said dispersion is prepared by wet granulating a mixture comprising the compound of Formula I and citric acid with water in the presence of a water soluble matrix polymer.

12. The formulation of claim 11 wherein said compound of Formula I comprises about 30 wt. % of said dispersion, and said dispersion comprises about 40 wt. % of said formulation.

13. A method of providing A2a- antagonist therapy to patients in need thereof who are also receiving proton-pump inhibiting therapy, said method comprising orally administering a therapeutic amount of the formulation of claim 1 to said patient.

14. A method of treating Parkinson's disease by administering a formulation according to claim 9 to a patient in need thereof.

15. A formulation comprising:
(a) a dispersion comprising:
  (i) a water soluble matrix polymer;
  (ii) a compound of Formula I:

Formula I and
  (iii) citric acid,
  wherein, at least about 70 mole % of said compound of Formula I is in the form of a citrate salt within the dispersion;
(b) at least one acidifying agent; and
(c) at least one solubilizing agent.

16. A formulation of claim 15, wherein said dispersion comprises:
(a) about 50 wt. % of a 3:2 wt./wt. ratio of a compound of Formula I, including the amount which is converted to a citrate salt, and citric acid, including the amount present in the citrate salt of the compound of Formula I; and
(b) the balance a water soluble polyvinylpyrolidone/vinyl acetate copolymer.

* * * * *